(12) United States Patent
Prasad et al.

(10) Patent No.: US 7,364,754 B2
(45) Date of Patent: Apr. 29, 2008

(54) CERAMIC BASED NANOPARTICLES FOR ENTRAPPING THERAPEUTIC AGENTS FOR PHOTODYNAMIC THERAPY AND METHOD OF USING SAME

(75) Inventors: Paras Prasad, Williamsville, NY (US); Indrajit Roy, Baltimore, MD (US); Earl J. Bergey, South Dayton, NY (US); Tymish Y. Ohulchansky, Kenmore, NY (US); Haridas Pudavar, North Tonawanda, NY (US)

(73) Assignee: Research Foundation of the State University of New York, Amherst, NY (US)

( * ) Notice: Subject to any disclaimer, the term of this patent is extended or adjusted under 35 U.S.C. 154(b) by 810 days.

(21) Appl. No.: 10/764,677

(22) Filed: Jan. 26, 2004

(65) Prior Publication Data

US 2004/0180096 A1    Sep. 16, 2004

Related U.S. Application Data

(60) Provisional application No. 60/442,237, filed on Jan. 24, 2003.

(51) Int. Cl.
*A61K 9/14*     (2006.01)
*A61K 31/57*    (2006.01)

(52) U.S. Cl. .................... 424/489; 424/489; 424/495; 424/499; 514/9; 514/171; 514/178

(58) Field of Classification Search ............... 424/489, 424/495, 499; 514/9, 171, 178
See application file for complete search history.

(56) References Cited

OTHER PUBLICATIONS

Tapan Kumar Jain, Indrajit Roy, Tapas K. De, and Amarnath Maitra; Nanometer silica particles encapsulating active compounds: A Novel ceramic drug carrier, J. Am. Chem. Soc. 120, 11092-11095, 1998.*

Arriagada, et al., *Synthesis of Nanosize Silica in Aerosol OT Reverse Microemulsions*, Journal of Colloid and Interface Science, 1995, 170, pp. 8-17.
Nass, et al., *Synthesis of an alumina coating from chelated aluminium alkoxides*, Journal of Non-Crystalline Solids, May 1, 1990, V. 121, Issues 1-3, pp. 329-333.
Badley, et al., *Surface Modification of Colloidal Silica*, Langmuir, 1990, 6, pp. 792-801.
Lal, et al., *Silica Nanobubbles Containing an Organic Dye in a Multilayered Organic/Inorganic Heterostructure with Enhanced Luminescence*, Chem. Mater, 2000, V. 12, pp. 2632-2639.
Kumar, et al., *Nanometer Silica particles Encapsulating Active Compounds: A Novel Ceramic Drug Carrier*, J. Am. Chem. Soc., 1998, 120, pp. 11092-11095.
Avnir, et al., *Enzymes and Other Proteins Entrapped in Sol-Gel Materials*, Chem. Mater., 1994, 6, pp. 1605-1614.
Taillefer, et al., *In-vitro and in-vivo evaluation of pH-responsive polymeric micelles in a photodynamic cancer therapy model*, Journal of Pharmacy and Pharmacology, 2001, 53, pp. 155-166.
Chang, et al., *Kinetics of Silica Particle Formation in Nonionic W/O Microemulsions from TEOS*, AIChE Journal, Nov. 1996, vol. 42, No. 11, pp. 3153-3163.

* cited by examiner

*Primary Examiner*—Michael G. Hartley
*Assistant Examiner*—Jagadishwar Samala
(74) *Attorney, Agent, or Firm*—Hodgson Russ LLP

(57) ABSTRACT

The present invention provides methods and compositions for photodynamic therapy. The composition comprises ceramic nanoparticles in which a photosensitive drug/dye is entrapped. The ceramic nanoparticles are made by formation of a micellar composition of the dye. The ceramic material is added to the micellar composition and the ceramic nanoparticles are precipitated by alkaline hydrolysis. The precipitated nanoparticles in which the photosensitive dye/drug is entrapped can be isolated by dialysis. The resulting drug doped nanoparticles are spherical, highly monodispersed, and stable in aqueous system. Irradiation with light of suitable wavelength of the photosensitizing drug entrapped inside nanoparticles resulted in generation of singlet oxygen, which was able to diffuse out through the pores of the ceramic matrix. The drug loaded ceramic nanoparticles of the present invention can be used as drug carriers for photodynamic therapy.

5 Claims, 8 Drawing Sheets

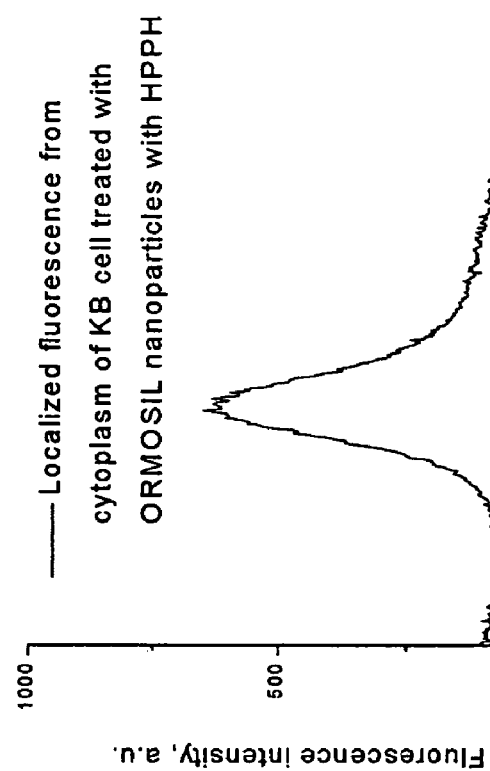
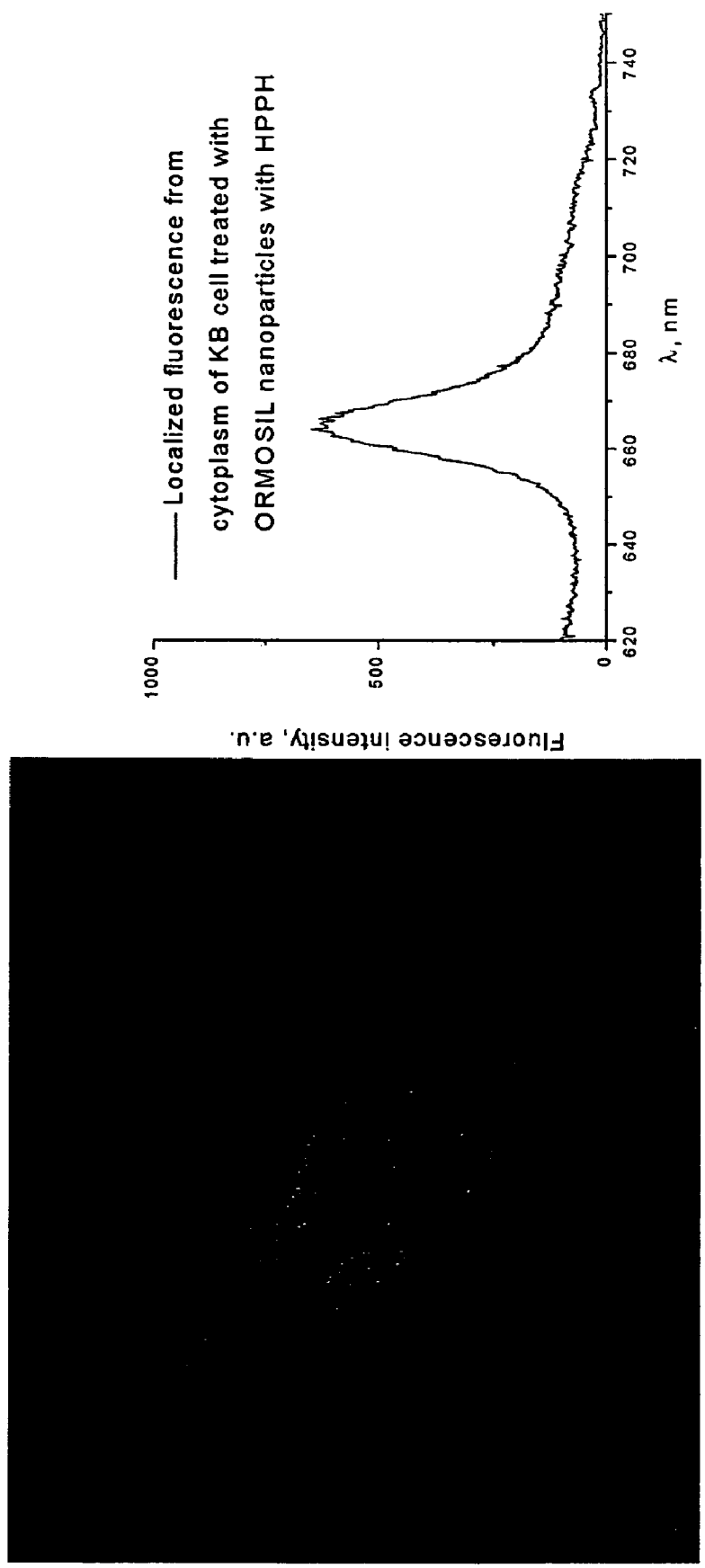
Figure 7B
Figure 7A

CERAMIC BASED NANOPARTICLES FOR ENTRAPPING THERAPEUTIC AGENTS FOR PHOTODYNAMIC THERAPY AND METHOD OF USING SAME

This application claims priority to U.S. Provisional application No. 60/442,237, filed on Jan. 24, 2003, the disclosure of which is incorporated herein by reference.

FIELD OF THE INVENTION

The present invention relates generally to the field of photodynamic therapy and more particularly to a novel drug-carrier system for photodynamic therapy.

DISCUSSION OF RELATED ART

Photodynamic Therapy (PDT) is an emerging modality for the treatment of a variety of oncological, cardiovascular, dermatological and ophthalmic diseases [1,2]. PDT for cancer is based on the concept that light sensitive species or photosensitizers (PS) can be preferentially localized in tumor tissues upon systemic administration [2,3]. When such photosensitizers are irradiated with an appropriate wavelength of visible or near infra-red (NIR) light, the activated molecules pass on their energy to surrounding molecular oxygen. This results in the formation of reactive oxygen species (ROS), like singlet oxygen ($^1O_2$) or free radicals. ROS are responsible for oxidizing various cellular membranes including plasma, mitochondria, lysosomal and nuclear membranes etc., resulting in irreversible damage of cells [2-6]. Under appropriate conditions, PDT offers the advantage of an effective and selective method of destroying diseased tissues without damaging adjacent healthy ones [3].

However, most photosensitizing drugs (PS) are hydrophobic, i.e. poorly water soluble, and therefore, preparation of pharmaceutical formulations for parenteral administration is highly hampered [2-7]. In order to overcome this difficulty, different strategies have evolved to enable the stable dispersion of these drugs into aqueous systems, often, by means of a delivery vehicle. Upon systemic administration, such drug-doped carriers are preferentially taken up by tumor tissues by the virtue of the 'Enhanced Permeability and Retention (EPR) Effect [2, 8-10]. The carriers include oil-dispersions (micelles), liposomes, polymeric micelles, hydrophilic drug-polymer complexes, etc. Oil-based formulations (micellar systems) using non-ionic poloxyethylated castor oils (e.g. Tween-80, Cremophor-EL, CRM, etc.) have shown enhanced drug loading and improved tumor uptake, presumably due to interaction with plasma lipoproteins in blood [11-13]. However, such emulsifying agents are also reported to elicit acute hypersensitivity (anaphylactic) reactions in vivo [14,15]. Liposomes are concentric phospholipid bilayers encapsulating aqueous compartments, which can contain hydrophilic and lipophilic drugs [2]. Although the tumor-uptake of liposomal formulation of drugs is better than that of simple aqueous dispersions, they suffer from poor drug loading and increased self-aggregation of the drug in the entrapped state [2, 16-18]. Liposomes are also prone to opsonization and subsequent capture by the major defense system of the body (Reticulo-Endothelial System, or RES) [18]. Recently, drugs incorporated inside pH sensitive polymeric micelles have shown improved tumor phototoxicity compared to CRM formulations in vitro, however in-vivo studies showed poor tumor regression and increased accumulation in normal tissues [7,19,20].

Hydrated ceramic based nanoparticles, doped with photosensitive drugs, carry the promise of solving the problems associated with free as well as polymer-encapsulated drugs. Such ceramic particles have a number of advantages over organic polymeric particles. First of all, the preparative processes involved, which are quite similar to the well known sol-gel process, require simple and room temperature conditions [21,22]. These particles can be prepared with desired size, shape and porosity, and are extremely stable [22]. Their ultra low size (less than 50 nm) can help them evade capture by the RES. In addition, there are no swelling or porosity changes with change in pH, and these particles are not vulnerable to microbial attack [23]. These particles also effectively protect doped molecules (enzymes, drugs etc.) against denaturation induced by extreme pH and temperature [24]. Such particles, like silica, alumina, titania etc. are also known for their compatibility in biological systems [24,25,26]. In addition, their surfaces can be easily functionalized with different groups [26,27], and therefore they can be attached to a variety of monoclonal antibodies and other ligands in order to target them to desired sites in vivo.

Although synthesis of ceramic nanoparticles, mostly but not exclusively based on silica, has been extensively reported in literature [28-30], their application in drug delivery has not yet been fully exploited. Thus, there is an ongoing need to develop novel drug delivery systems for PDT therapy.

SUMMARY OF THE INVENTION

This invention provides compositions and methods useful for photodynamic therapy. The compositions of the present invention comprise ceramic based nanoparticles in which one or more therapeutic agents are entrapped.

This invention also provides a method for the synthesis of the ceramic based nanoparticles in which one or more therapeutic agents are entrapped. When synthesized by the method of the present invention, the particles were found to be spherical and highly monodispersed.

In one embodiment, this invention provides a method for the synthesis of photosensitizer dye/drug doped silica-based nanoparticles (diameter ~30 nm), by controlled alkaline hydrolysis of a ceramic material (such as triethoxyvinylsilane (VTES)) in micellar media.

In one embodiment, the photosensitive drug/dye used was 2-devinyl-2-(1-hexyloxyethyl)pyropheophorbide (HPPH), an effective photosensitizer which is in Phase I/II clinical trials at Roswell Park Cancer Institute, Buffalo, N.Y., USA [32,33]. Although the particle matrix does not interfere with the visible absorption spectra of the entrapped photosensitizing drug, the quenching of fluorescence of the drug was found to be largely prevented in aqueous media. Singlet oxygen detection experiments revealed that the entrapped photosensitizer is able to interact with the surrounding molecular oxygen and the singlet oxygen generated is able to permeate out of the silica matrix. Such doped particles are actively taken up by tumor cells and light irradiation of suitable wavelength resulted in irreversible destruction of such impregnated cells. Accordingly, the ceramic-based particles of the present invention can be used as carriers for photodynamic therapy drugs.

BRIEF DESCRIPTION OF THE DRAWINGS

FIG. 1 is a representation of a Transmission Electron Micrograph of HPPH doped Silica-based nanoparticles showing highly monodispersed particles with average diameter of 30 nanometers.

FIG. 7 is a representation of two-photon confocal fluorescence image of a single tumor (KB) cell treated with HPPH doped nanoparticles. The inset shows localized fluorescence spectra from the cytoplasm of the treated cell.

DETAILED DESCRIPTION OF THE INVENTION

Figure 1:
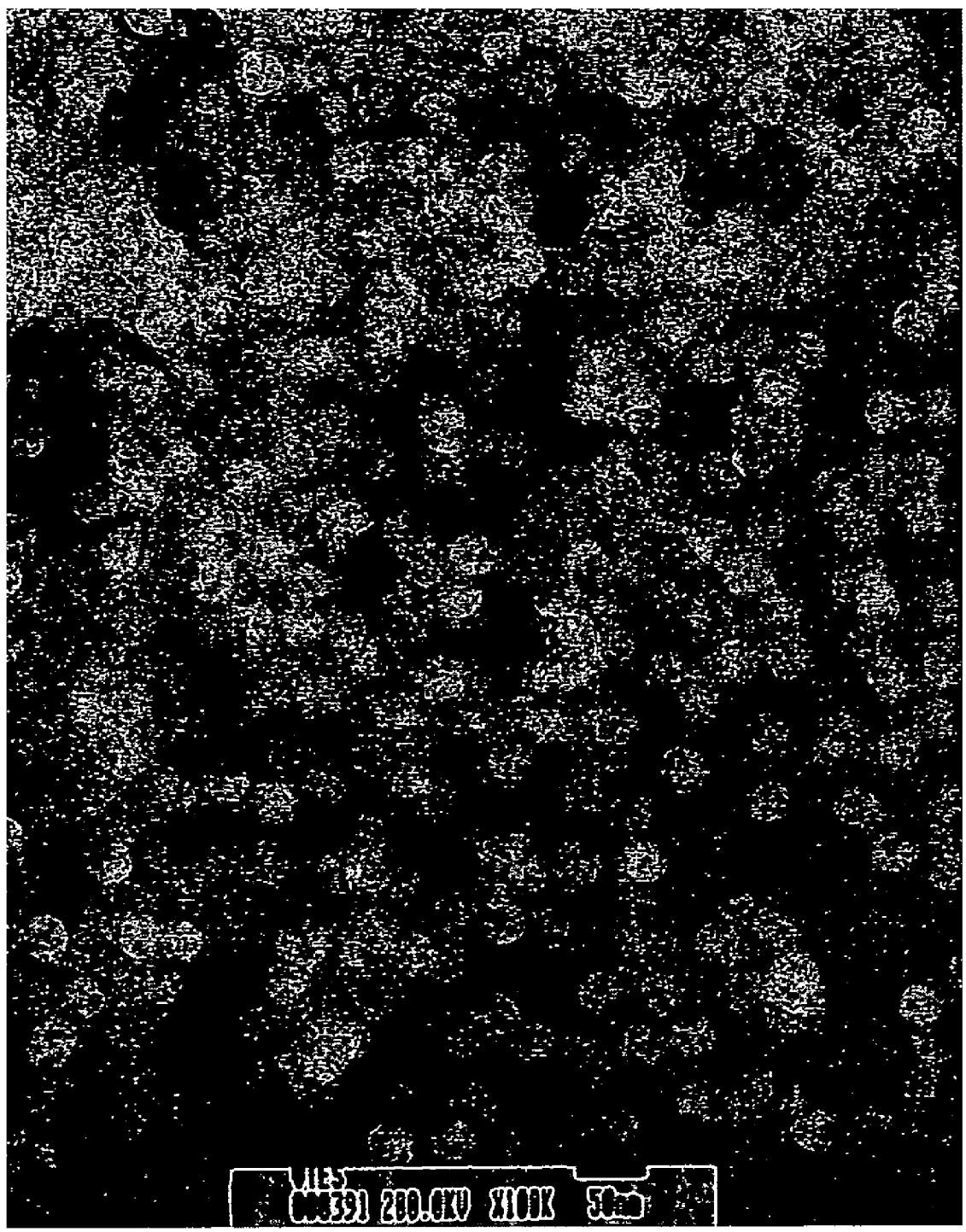

The present invention provides ceramic nanoparticles in which one or more therapeutic agents are entrapped. The present invention also provides a method for the synthesis and use of the ceramic particles loaded with one or more therapeutic agents. The term "nanoparticles" is used herein to indicate particles that are 100 nm of less in diameter.

The ceramic nanoparticles of the present invention can be used to deliver therapeutic agents such as photosensitive drugs or dyes to cells for photodynamic therapy. The drugs may be hydrophobic and hydrophilic.

In one embodiment, the silica particles useful in the present invention are organically modified silicate (ORMOSIL) nanoparticles loaded with a hydrophobic photosensitive (also referred to herein as photosensitizer) drug. To prepare the nanoparticles, the photosensitizer is entrapped inside the non-polar core of sodium bis(2-ethylhexyl)sulfosuccinate (AOT)/1-butanol/water micelles which are dissolved in alkoxy-organosilane (such as triethoxyvinylsilane (VTES)) and precipitated by alkaline hydrolysis (such as by ammonia, ammonium compounds or amine containing compounds) under gentle conditions (such as stirring at room temperature for 24 hours). The precipitated materials and surfactant are removed by dialysis. The dialysis can be carried out for prolonged period of time (such as 50 hours) indicating that the entrapped agent has stable dispersion over a long time.

The main advantage of ORMOSIL nanoparticles over other nanoparticles is that the presence of both hydrophobic and hydrophilic groups on the precursor alkoxy-organosilane helps them to self-assemble both as normal micelles and reverse micelles under appropriate conditions. The resulting micellar (and reverse micellar) cores can be used for entrapping biomolecules like drugs, proteins, etc. Such a system has a number of advantages including: (a) they can be loaded with both hydrophilic as well as hydrophobic dyes, (b) they can be precipitated in oil-in-water microemulsions so that corrosive solvents like cyclohexane and complex purification steps like solvent evaporation, ultra-centrifugation etc., can be avoided (c) their organic group can be further modified for the attachment of targeting molecules, and (d) they may be can be possibly bio-degraded through the biochemical decomposition of the Si—C bond. The presence of the organic group also reduces the overall rigidity and density of the particle, which is expected to enhance the stability of such particles in aqueous systems against precipitation.

Spherical, monodisperse particles of colloidal silica can be conveniently prepared by hydrolysis of tetraalkyl silane. This method, commonly referred to as the 'sol-gel' method, can be further extended in the synthesis of organically modified silica (ORMOSIL) particles, where the precursor alkoxysilane molecules also include one or two organic groups. The incorporation of organic groups modify the final structure of the silica network, e.g. leading to the formation of mesoporous matrices, characterized by a network structure of ordered and uniform porosity. Such porous matrices can host a number of optically as well as biologically active molecules like fluorescent dyes, proteins, anticancer drugs, image contrast agents, etc.

For using the ceramic particles of the present invention, the drug loaded particles can be administered locally or systemically. Local administration can be effected, for example, by injection of a composition comprising the drug/dye loaded ceramic particles proximate to the target tissues or intratumoral. In local treatment of superficial tumors, the nanoparticles can be topically administered by incorporating into standard topical compositions involving lotions, suspension, or pastes. Systemic administration can be implemented by intravenous, subcutaneous, intramuscular, intraperitoneal or rectal route. Formulations for these modes of administration are well known in the art; exemplary formulations are described, for example, in Remmington's Pharmaceutical Sciences, Easton, Pa.:Mack Publishing Co.

The nanoparticles entrapping a drug/dye can be administered in the form of a composition made up in a suitable form appropriate for the desired use; e.g., oral, parenteral, or topical administration. Suitable dosage forms for oral use include suspensions, dispersion, emulsions in the form of tablets, dispersible powders, granules, capsules, syrups, and elixirs. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate. Dosage forms suitable for parenteral administration include ceramic nanoparticles in suspensions, dispersions, emulsions, and the like.

In general, ceramic nanoparticles are highly stable, and may not release any encapsulated biomolecules even at extreme conditions of pH and temperature [24]. Conventional drug delivery methods require the carrier vehicle to free the encapsulated drug in order to elicit the appropriate biologic response [3]. However, this is not required when macromolecular carrier molecules are used for the delivery of photosensitizing drugs in PDT [3, 31]. In the present invention, we have developed ceramic-based nanoparticles as carriers of photosensitizing drugs for applications in PDT. Their porous matrix of the nanoparticles is permeable to molecular oxygen as well as reactive oxygen species (singlet oxygen and free radicals) and the nanoparticles do not release any significant amounts of entrapped drugs into an aqueous environment. Therefore, the desired photodestructive effect of the drug can be maintained even in the entrapped form.

By the method of the present invention, silica based nanoparticles, doped with a water-insoluble photosensitizing anticancer drugs such as HPPH, can be synthesized in micellar media. The doped particles, with a unimodal size distribution of 30 nm, can be formulated as stable aqueous dispersion. Although the drug is embedded inside the particle matrix, it can be sensitized by irradiation with light of appropriate wavelength, and the generated singlet oxygen can diffuse out of the particle matrix. Such doped nanoparticles are actively taken up by tumor cells and light irradiation of such impregnated cells results in significant cell-death. These observations demonstrate that various ceramic based matrices can be used as drug carriers for Photodynamic Therapy. The particles of the present invention can be used as injectable formulations for safe and efficient trafficking to tumor tissues in vivo.

In one embodiment, the specific tumor-targeting ligands can be attached to the surface of the ceramic nanoparticles. Recently, our group has synthesized silica based nanoparticles which encapsulate a magnetic core [39]. These particles were functionalized with a peptide hormone targeting agent (lutinizing hormone releasing hormone (LH—RH)). The resulting 'nanoclinic' was shown to selectively target LH—RH receptor-positive tumor cells. Exposure to a DC magnetic field then resulted in the selective magnetocytolysis of the receptor positive cells only (U.S. Pat. No. 6,514,481, incorporated herein by reference). Thus, the ceramic surface of the nanoparticles of the present invention can be functionalized with different ligands in order to target the particles to tumor-cells containing such ligand-specific receptors.

The present invention is further described by way of examples presented below which are intended to be illustrative and not restrictive in any way.

EXAMPLE 1

This example describes the preparation of the drug-loaded silica nanoparticles. To illustrate this embodiment, silica particles loaded with HPPH were synthesized. Surfactant Aerosol OT (AOT, 98%), Co-surfactant n-Butanol (99.8%), and Triethoxyvinylsilane (VTES, 97%), were purchased from Aldrich. MTT and isopropanol are a product of Sigmna. Deuterium oxide (99.9 Atom % D) was obtained from Isotec Inc., USA. Dye/Drug HPPH 2-devinyl-2-(1-hexyloxyethyl)pyropheophorbide[38] was a kind gift from Dr. Tom Dougherty, Roswell Park Cancer Institute, Buffalo, N.Y. Dye anthracenedipropionic acid-disodium salt (ADPA) was purchased from Molecular Probes, USA. Cell-Culture products like medium MEM-alpha, 5% Fetal Bovine Serum (FBS), Phosphate Buffered Saline (PBS) etc. were purchased from GIBCO, USA. All the above chemicals were used without any further purification.

Figure 2:
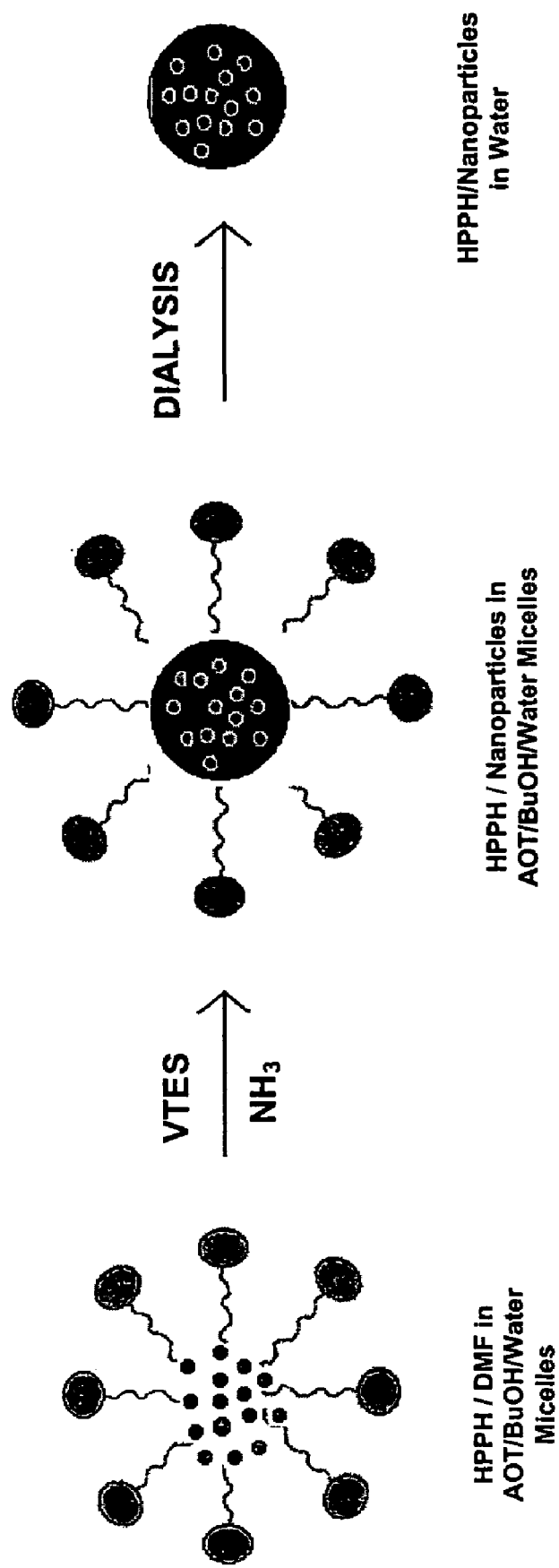
FIG. 2 is a schematic representation of the synthesis and purification of HPPH doped Silica-based nanoparticles in micellar medium.

The nanoparticles, both void and drug-loaded, were synthesized in the non-polar core of AOT/n-Butanol/Water micelles, as shown schematically in FIG. 2. The micelles were prepared by dissolving 0.44 g of AOT and 800 µL (0.56 g) of n-butanol in 20 mL of double distilled water by vigorous magnetic stirring. To the resulting clear solution, 40 µL of HPPH in DMF (15 mM) and 10 µL of pure DMF were dissolved by magnetic stirring (in case of void ormosil particles, 50 µL of DMF and no HPPH was added). Then to the micellar system, 200 µL of neat triethoxyvinylsilane (VTES) was mixed and allowed to stir for about one hour, or till the solution becomes clear. After that, 10 µL of aqueous ammonia (10 M) solution was added and the system was allowed to stir for about twenty hours. The entire reaction was carried out at room temperature. At the end of the process, a bluish-white translucency indicating the formation of nanoparticles was observed. After the formation of drug-doped nanoparticles, surfactant AOT and co-surfactant n-Butanol were completely removed by dialyzing the solution against water in a 12-14 kD cut-off cellulose membrane (from Spectrum Laboratories, Inc., USA) for 40 hours. The dialyzed solution was then filtered through a 0.2 Micron cut-off membrane filter (Nalgene, USA), and was used for further experimentation.

Transmission Electron Microscopy (TEM) was employed to determine the morphology and size of the resulting aqueous dispersion of nanoparticles, using a JEOL JEM 2020 Electron Microscope, operating at an accelerating voltage of 200 kV. The results are shown in FIG. 1 as a Transmission Electron Microscopy (TEM) picture of the drug loaded nanoparticles. The particles are spherical, having unimodal size distribution, with an average size of 30 nanometers (as prepared with the above protocol).

EXAMPLE 2

Figure 3:
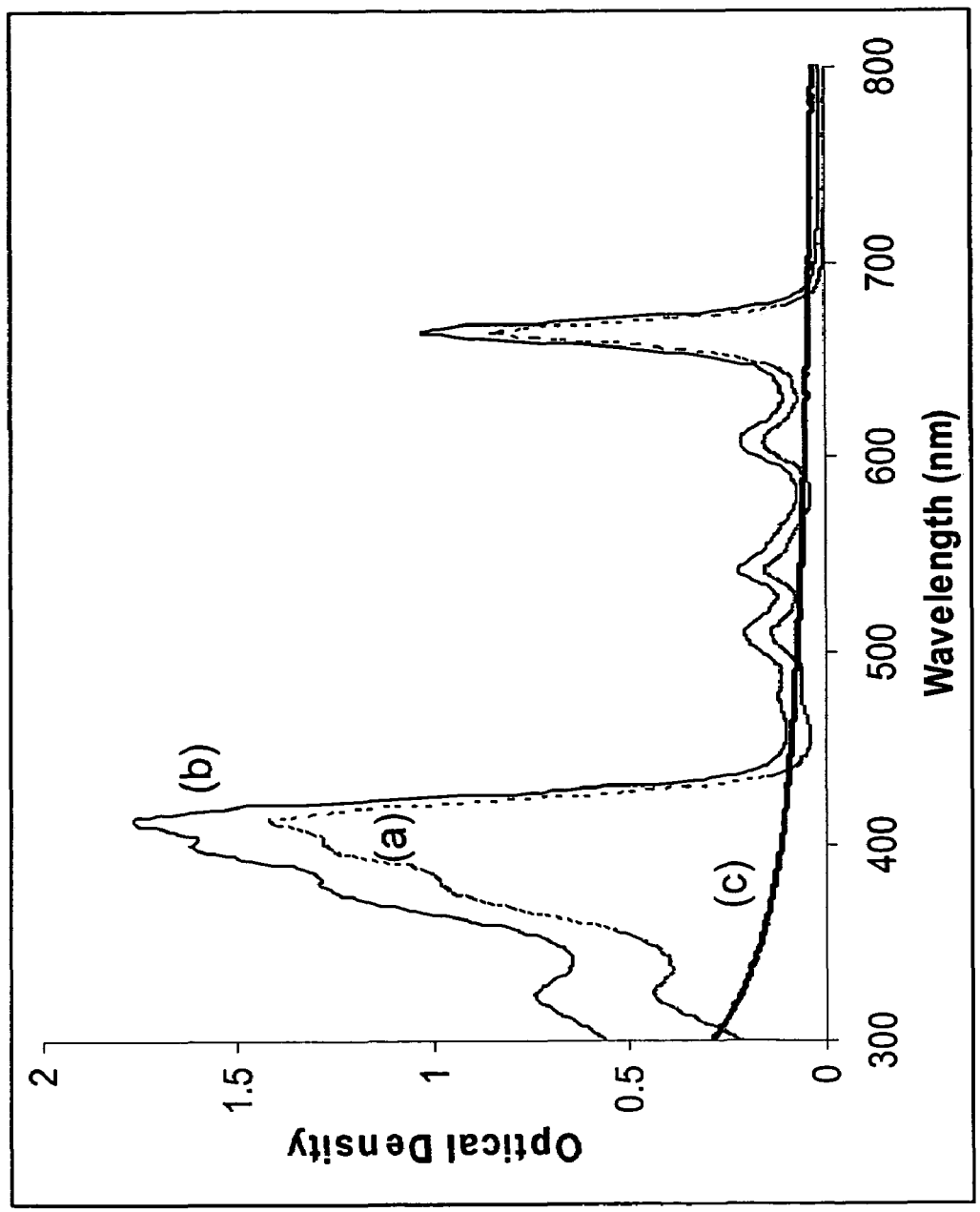
FIG. 3 is a representation of UV-Visible absorption spectra of (a) HPPH in AOT/BuOH/Water micelles, (b) HPPH doped in silica nanoparticles and (c) void silica nanoparticles.

This example demonstrates that the emission characteristics of the entrapped drug is the same as the unentrapped drug. To illustrate this embodiment, UV-Visible absorption Spectra of the silica particles in which the drug was entrapped and free drug was recorded on a Shimadzu (Columbia, Md.) UV-3101 PC Spectrophotometer, using 1 cm thick Quartz Cuvettes and fluorescence Spectra was recorded on a Shimadzu RF 5000U Spectrofluorimeter using 1 cm thick Quartz cuvette. The UV-Visible absorption spectra of HPPH, in AOT/BuOH/Water micelles as well as entrapped inside nanoparticles show the same peak positions for the two (FIG. 3). This demonstrates that there is no shift in peak position of HPPH upon entrapment inside nanoparticles. A control experiment, using void nanoparticles, shows virtually no absorption in the visible and Near Infra-Red (NIR) wavelength region (600-900 nm), which is the region of interest (Therapeutic Region) in PDT due to the high tissue penetration of light. Therefore, such particles can be effectively used in PDT, as they do not interfere with the therapeutic light used for excitation of photosensitive anticancer drugs.

Figure 4:
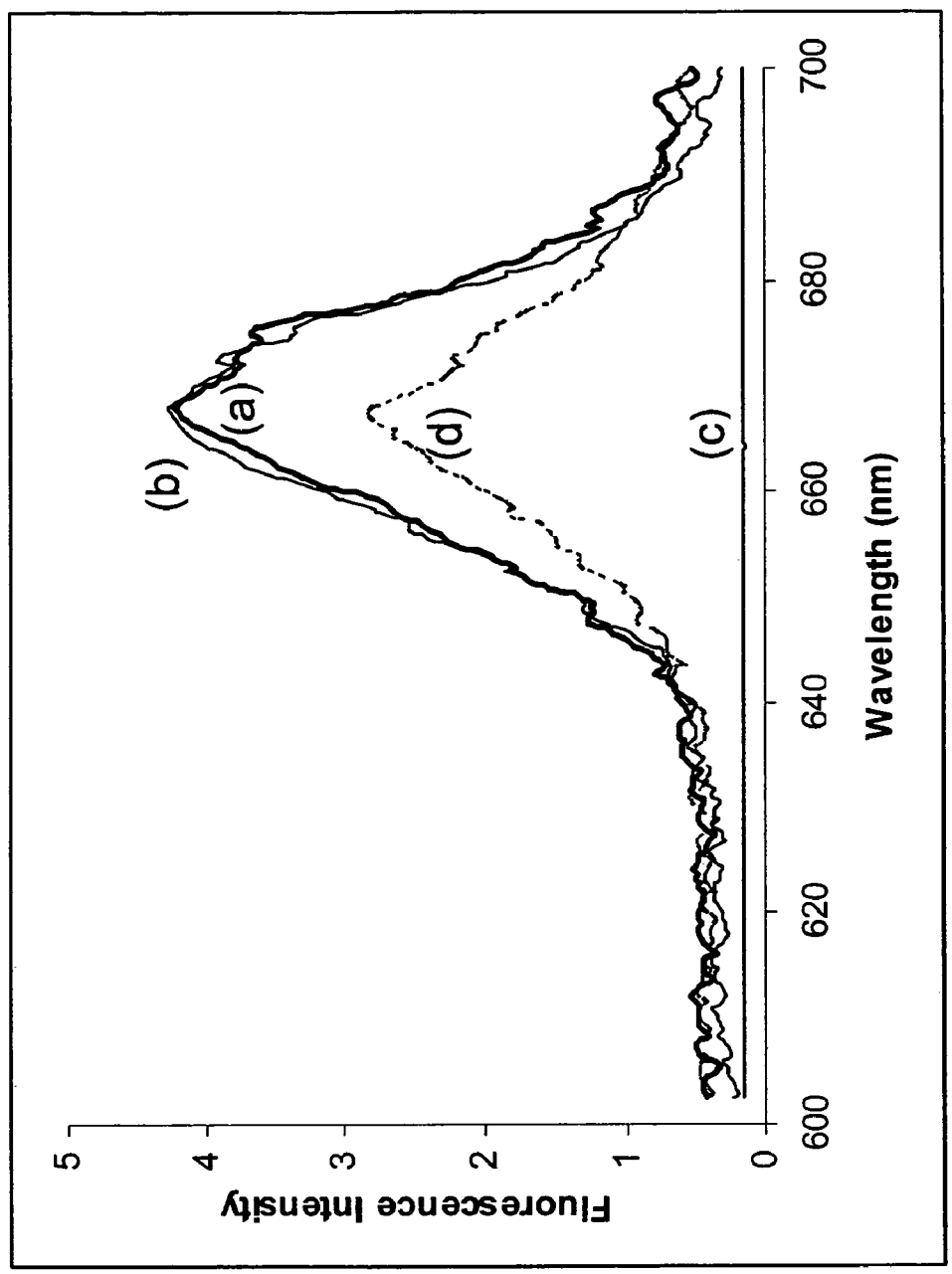
FIG. 4 is a representation of fluorescence emission spectra of (a) HPPH in AOT/BuOH/Water micelles before dialysis, (b) HPPH doped in silica nanoparticles before dialysis, (c) HPPH in AOT/BuOH/Water micelles after dialysis, and (d) HPPH doped in silica nanoparticles after dialysis. Excitation wavelength is 414 nm.

FIG. 4 represents the fluorescence emission spectra of HPPH, in AOT/BuOH/Water micelles as well as entrapped inside nanoparticles. The spectra for both the samples, at an excitation wavelength of 414 nm, were recorded before and after dialysis against distilled water (which effectively removes the surfactant and co-surfactant molecules used). While the emission for HPPH, in micelles as well as nanoparticles, are almost similar before dialysis, substantial difference between the two can be observed after dialysis.

While the emission intensity from the nanoparticle doped HPPH is still significant (almost 75% of the intensity obtained before dialysis), practically no emission is observed from the HPPH/'micelles' after dialysis. This can be explained by the fact that HPPH, being a non-polar molecule, aggregates in polar solvents and therefore its fluorescence gets self-quenched. As long as HPPH molecules are inside the non-polar core of micelles, they remain separated, but with the removal of surfactants, the molecules come increasingly in contact with the aqueous surrounding, and begin to aggregate. But in case of nanoparticle-doped HPPH, the drug molecules can be visualized as discretely embedded in the particle matrix (refer to FIG. 1), and therefore, exposure to aqueous system does not result in their aggregation and significant loss of emission intensity. This property of entrapped drugs/dyes of resistance to self-quenching in aqueous media can be exploited to fabricate nanoprobes for imaging in biological systems.

EXAMPLE 3

This example demonstrates the generation of singlet oxygen by the entrapped drug as detected by phosphorescence spectra. Detection of singlet oxygen ($^1O_2$) has been extensively reported by its phosphorescence emission spectra at 1270 nm [34, 35]. Since the lifetime of $^1O_2$ in water is very low (2-5 μs) and hence its detection by the above method is very difficult, we have used Deuterium Oxide ($D_2O$) owing to the enhanced lifetime (50-60 μs) of $^1O_2$ in this solvent [36]. In a typical experiment, 3 mL of 22.5 μM HPPH, entrapped in nanoparticles dispersed in $D_2O$, was used. HPPH solubilized in AOT/BuOH/$D_2O$ micelles and void nanoparticles in $D_2O$ were used as positive and negative controls, respectively. A SPEX 270M Spectrometer (Jobin Yvon) equipped with In—Ga—As photodetector (Electro-Optical Systems Inc., USA) was used for recording singlet oxygen phosphorescence emission spectra. A solid-state diode-pumped laser (Verdi, Coherent) was used as a source of excitation (532 nm). A 1 cm thick square quartz cuvete with sample solutions was placed directly in front of the entrance slit of the spectrometer and emission signal was collected from the side of cuvette at 90-degrees relative to exciting laser beam. As additional NIR long wave edge filter (Andover Corp., USA) was also placed before the photodetector.

Figure 5:
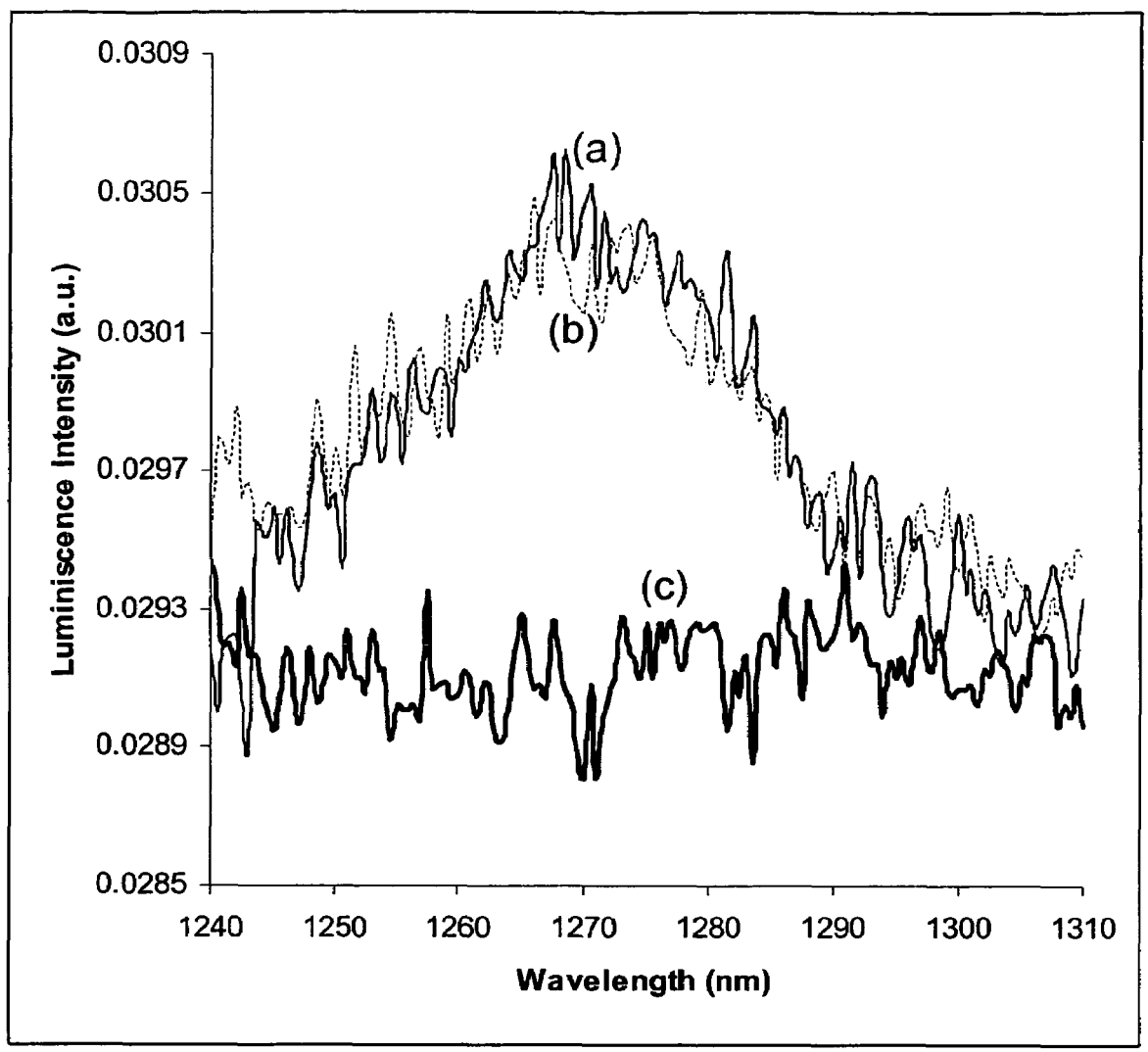
FIG. 5 is a representation of Phosphorescence emission spectra of generated singlet oxygen at 1270 nm of (a) HPPH in AOT/BuOH/$D_2O$ micelles (solid line), (b) HPPH doped in silica nanoparticles dispersed in $D_2O$, and (c) Void silica nanoparticles in $D_2O$.

The results demonstrate that since ceramic matrices are generally porous, photosensitizing drugs entrapped within them can interact with molecular oxygen by diffusion of oxygen through these pores. Any reactive oxygen species (ROS), formed as a result of interaction of oxygen with the excited photosensitizer, will diffuse out of the porous matrix, into the surrounding environment, where it can be detected. We have studied the generation of singlet oxygen, the ROS which evolves from HPPH, by its phosphorescence emission spectra at 1270 nm. FIG. 5 shows the spectra for HPPH, solubilized in micelles as well as entrapped in nanoparticles. Both the spectra show peaks at 1270 nm, indicating the evolution of singlet oxygen in both the cases. Control spectrum, ran with void nanoparticles, shows no phosphorescence peak. This demonstrates that singlet oxygen is indeed generated by photosensitized BPPH in the entrapped state, which can diffuse out through the pores of the ceramic matrix to interact with the surrounding environment.

EXAMPLE 4

This example demonstrates the generation of singlet oxygen by the entrapped drug as detected by a chemical method using disodium salt of anthracenedipropionic acid (ADPA) as detector. In addition to Phosphorescence Spectra, generation of singlet oxygen was also detected chemically, using disodium salt of ADPA (9,10-anthracenedipropionic acid) as singlet oxygen sensor [36]. Disodium-ADPA (a water-soluble anthracene-derivative) is bleached to its corresponding endoperoxide on reaction with singlet oxygen, which was followed spectrophotometrically by recording the decrease in Optical Density at 400 nm ($\lambda_{max}$ of ADPA). In a typical experiment, 150 μL of disodium-ADPA in $D_2O$ (5.5 mM) was mixed with 3 mL of 15 μM HPPH (in AOT/$D_2O$ micelles as well as entrapped in nanoparticles in $D_2O$) in 1 cm thick Quartz Cuvettes. A control experiment was carried out with disodium-ADPA mixed with void nanoparticles dispersed in $D_2O$. The resulting solutions were irradiated with a 650 nm Laser Source (Solid-State Diode-Pumped Laser) and their Optical Densities were recorded every 10 minutes in a spectrophotometer.

Figure 6:
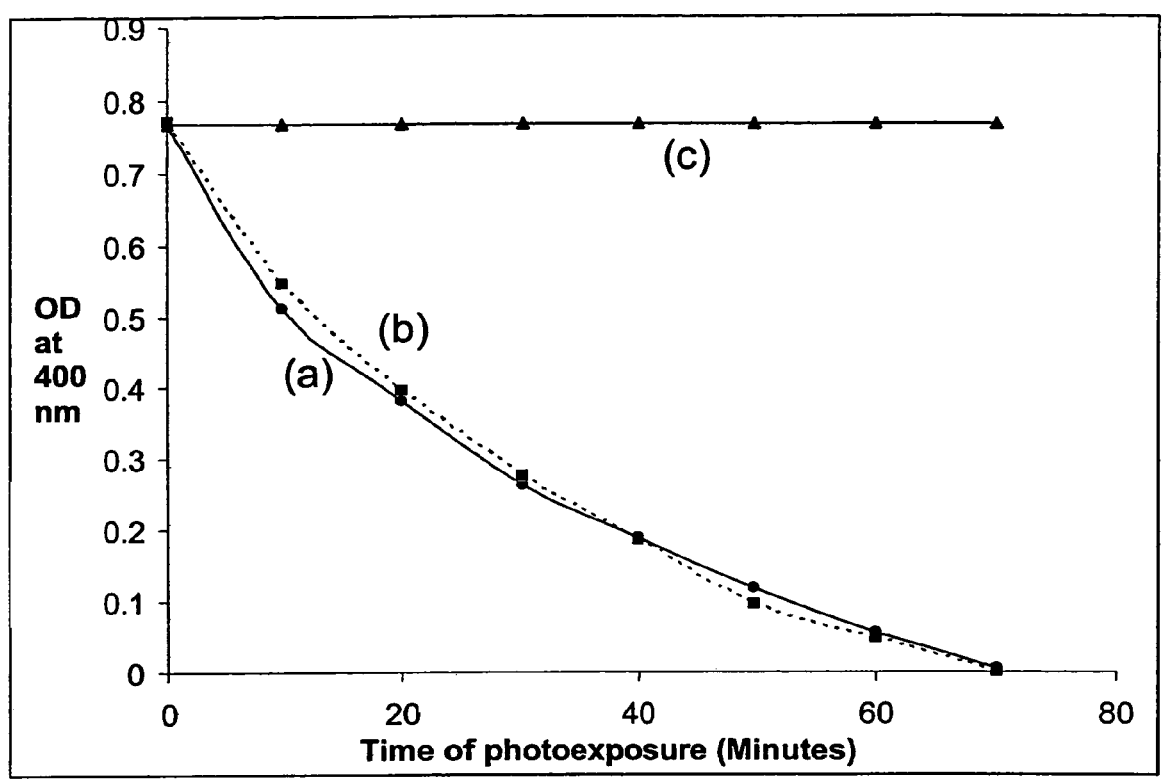
FIG. 6 is a representation of the time-dependent bleaching of dye ADPA (at $\lambda_{max}$ 400 nm) by generated singlet oxygen upon photo-irradiation by (a) HPPH in AOT/BuOH/$D_2O$ micelles, (b) HPPH doped in silica nanoparticles dispersed in $D_2O$, and (c) Void silica nanoparticles in $D_2O$.

FIG. 6 shows the time-dependent bleaching of ADPA, observed by the decrease in Optical Density (OD) at 400 nm (absorption maxima for ADPA), upon incubation with different samples and photo-exposure. The plots with HPPH, solubilized in micelles as well as doped in nanoparticles, show sharp fall in OD with time of light exposure, indicating ample evolution of singlet oxygen in both the cases. Plot with void nanoparticles incubated with ADPA showed no reduction in OD with time, indicating that the bleaching of ADPA is a result of generated singlet oxygen and not by the irradiated light.

EXAMPLE 5

This example demonstrates that the silica nanoparticles, in which a photosensitizer drug/dye is entrapped can be taken up by cells. For studying nanoparticle uptake, KB cell line (human epithelial oral carcinoma cells) was used. Cells were maintained at 37° C. (humidified 5% $CO_2$ atmosphere) in DMEM medium with 10% Fetal Bovine Serum (FBS). Monolayers of cells, in 3 ml of medium, were incubated with 100 μl of aqueous dispersion of HPPH (15 μM) doped nanoparticles for an hour in 60×15 mm tissue-culture plates. The cells were rinsed with sterile phosphate buffered saline (PBS), and directly observed under a confocal laser scanning microscope.

Having established the generation of cytotoxic singlet oxygen molecules by HPPH doped inside nanoparticles, we determined the uptake of such doped nanoparticles by tumor cells using fluorescence imaging technique. The two-photon fluorescence image of tumor (KB) cells (FIG. 7A) shows significant staining in the cytoplasm and membranes, indicating accumulation of nanoparticles in those regions. Localized spectra of the cytoplasm, shown in FIG. 7B show the characteristic emission peak for HPPH (665 nm), which effectively separates HPPH fluorescence from auto-fluorescence of such cells. The viability of such treated cells was verified by their morphology and it indicated the cells were alive even after 10 hours of staining.

EXAMPLE 6

This example demonstrates that the silica nanoparticles of the present invention can be used for photodynamic therapy. As an illustration, cell viability was studies in cells which had taken up the drug loaded silica nanoparticles with and without photoirradiation. For studying cell viability, UCI-107 (university of California, Irvine, Calif.) tumor cell line was used. Cells were maintained in MEM alpha Medium with 5% FBS at 37° C. (humidified 5% $CO_2$ atmosphere).

Prior to the experiment, 24-well plates were inoculated with cells (7.5×10⁵ cells/well) and incubated overnight. The medium was removed and the wells were rinsed three times using sterile PBS. After careful rinsing, 2 mls of fresh medium was replaced into each well. Pre-determined concentrations of the drug, as determined by Optical Density measurements, i.e. (a) 20 µM HPPH in 120 µL 0.25% Tween-80/Water micelles, (b) 20 µM HPPH encapsulated in 120 µL aqueous nanoparticle dispersion, (c) 120 µL 0.25% Tween-80/Water micelles, and (d) 120 µL aqueous void-nanoparticle dispersion, were added to designated wells at this time, and the plate was then returned to the incubator for two hours. The wells were rinsed three times with sterile PBS, and fresh medium was replaced at a volume of 2 mls/well. Immediately following medium replacement, the wells was exposed to a 650 nm light source (using solid-state diode-pumped laser) for 10 minutes each. After the completion of exposure to the light source, the plate was returned to the incubator overnight. Cell viability was estimated by means of the colorimetric MTT (3-(4,5-dimethylthiazol-2-yl)-2,5-diphenyltetrazolium bromide) assay [37]. MTT measures only viable living cells and absorbance at 570 nm is found to be directly proportional to the number of such cells. Briefly, MTT was dissolved in sterile PBS at a concentration of 5 mg/ml and added to each well at a volume of 200 µl/well. The plate was then incubated at 37° C. with 5% $CO_2$ for 4 hours. After incubation, medium containing MTT solution was carefully aspirated from all wells. 2 mls of a 0.1 N HCl in anhydrous isopropanol solution were added to each well to dissolve any purple MTT formazan crystals that formed. The resulting purple solution's absorbance was measured at 570 nm using a Bausch & Lomb Spectronic 601 spectrophotometer. Average absorbance of control cells, which were incubated with only serum supplemented medium, represents 100% cell survival. Four fold replicates were run per drug and light dose, and each experiment was repeated three times.

Figure 8:
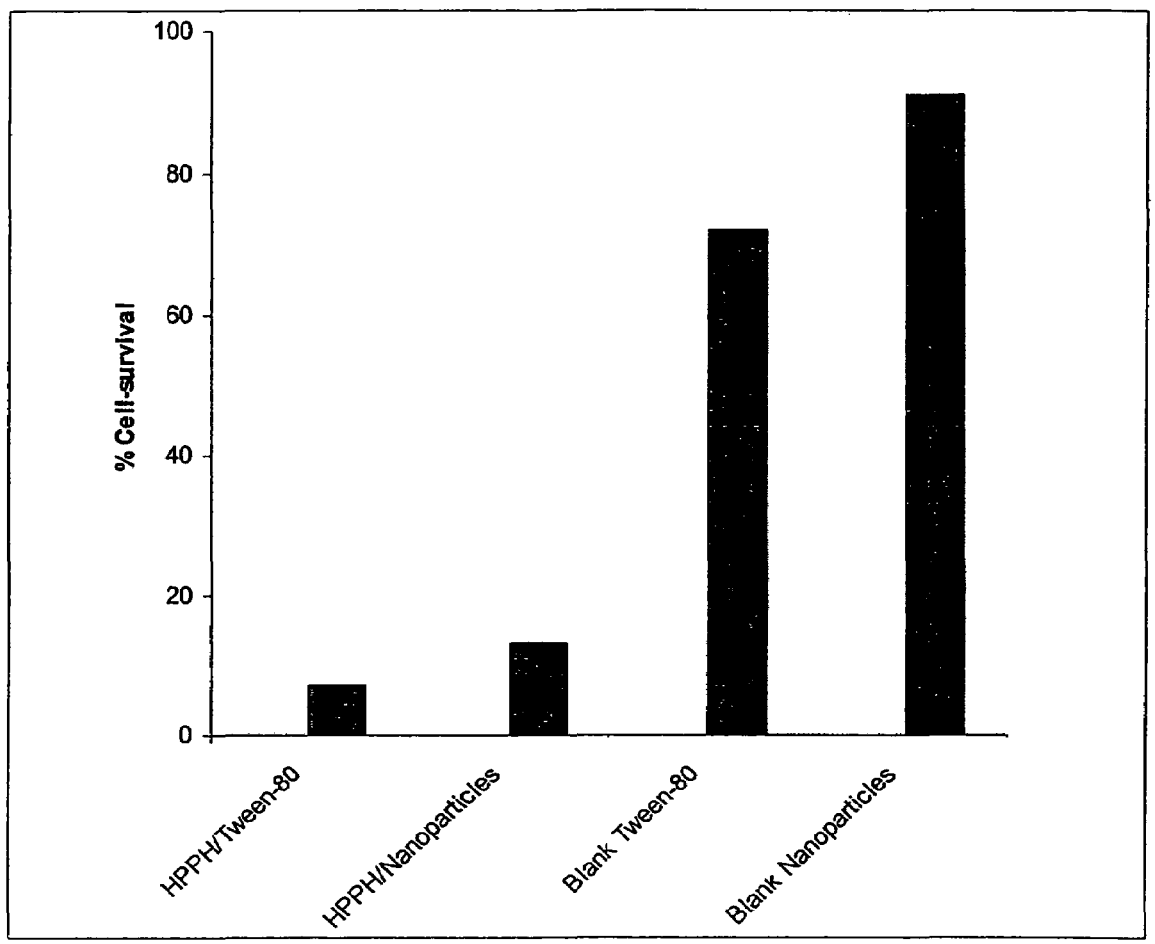
FIG. 8 is a representation of the percentage cell-survival of UCI-107 cells as assayed by MTT method.

The results in FIG. 8 show percentage of cell survival on treatment of UCI-107 tumor cells with various agents (relative to pure medium as control) and subsequent photo-activation. Significant cell-death can be observed for both HPPH in Tween-80 micelles (about 7% cell-survival) and HPPH doped in nanoparticles (about 11% cell-survival). In addition, substantial cellular toxicity can be observed for blank Tween-80 micelles, which is usually known to be a non-toxic surfactant, while blank nanoparticles have very little toxicity. In general, it can be concluded that HPPH doped nanoparticles are almost as effective a drug/carrier system as HPPH solubilized in Tween-80 micelles for killing tumor cells.

EXAMPLE 7

This example describes the use of nanoparticles of the present invention can be used in an animal. Female SCID mice carrying a human tumor can be injected intraperitoneally with HPPH doped nanoparitcles ($10^{14}$ particles per gram body weight). After injection, the animals can be housed for 24 h in single cages in absolute darkness. The mice can be anaesthesized with 5.5 µg fentanyl and 5.5 mg metomidat-hydrochloride (Janssen Cilag, Sulzbach, Germany) in 0.9% NaCl per 100 g body weight and the fur shaved once more before photoirradiation. The tumors can be exposed for 2 min to laser light of 532 nm with a power of 50 mW to deliver a total irradiation dose of 30 J/cm2 (ambient temperature 25° C.). The light can be delivered using a fiber optic light delivery system. Tumors of animals without photoirradiation can serve as controls. Assessment of tumor response can be determined by changes in size and histological morphology. Based on the description provided herein, the nanoparticles can be used for PDT in other individuals including humans.

Although the present invention is demonstrated through the examples presented herein, routine modifications of the various embodiments will be apparent to those skilled in the art and are intended to be within the scope of the invention as described in the specification and claims.

REFERENCES

1. Levy, J. G.; Obochi, M. *Photochem. Photobiol*. 1996, 64, 737-739.
2. Konan, Y. N.; Gruny, R.; Allemann, E. *J Photochem. Photobiol. B: Biology*. 2002, 66, 89-106.
3. Hasan, T.; Moor, A. C. E.; Ortel, B. *Cancer Medicine 5th Edition*. Hamilton, Ontario: B. C. Decker, Inc., 2000, p-489.
4. Dougherty, T. J. *Photochem. Photobiol*. 1987, 45, 879-889.
5. Kessel, D. *Drugs of Today*, 1996, 32, 385-396.
6. Ochsner, M. *J Photochem. Photobiol. B: Biology*. 1997, 39, 1-18.
7. Taillefer, J.; Jones, M. C.; Brasseur, N.; Van Lier, J. E.; Leroux, J. C. *J. Pharm. Sci*. 2000, 89, 52-62.
8. Juliano, R. L. *Adv. Drug Deliv. Rev*. 1998, 2, 31-54.
9. Steyger, P. S.; Baban, D. F.; Brereton, M.; Ulbrich, K.; Seymour, L. W. *J. Control. Release*. 1996, 39, 35-46.
10. Duncan, R. *J. Drug targ*. 1997, 5, 1-4.
11. Selman, S. H.; Garbo, G. M.; Keck, R. W.; Kreimer-Birnbaum, M. Morgan, A. R. *J. Urol*. 1987, 137, 1255-1257.
12. Kongshaug, M.; Moan, J.; Cheng, L. S.; Garbo, G. M.; Kolboe, S.; Morgan, A. R.; Rimington, C. *Int. J. Biochem*. 1993, 25, 739-760.
13. Woodburn, K.; Kessel, D. *J. Photochem. Photobiol. B. Biol*. 1994, 22,197-201.
14. Dye, D.; Watkins, J. *Br. Med. J*. 1980, 280, 1353.
15. Michaud, L. B. *Ann. Pharmacother*. 1997, 31, 1402-1404.
16. Damoiseau, X.; Schuitmaker, H. J.; Lagerberg, J. W. M.; Hoebeke, M. *J. Photochem. Photobiol. B Biol*. 2001, 60, 50-60.
17. Richter, A. M.; Waterfield, E.; Jain, A. K.; Canaan, J. A.; Allison, B. A.; Levy, J. G. *Photochem. Photobiol*. 1993, 57, 1000-1006.
18. Isele, U.; Schieweck, K.; Kessler, R.; Hoogevest, P. V.; Caparo, H. G. *J. Pharm. Sci*. 1995, 84,166-173.
19. Jones, M. C.; Leroux, J. C. *Eur. J. Pharm. Biopharm*. 1999, 48, 101-111.
20. Taillefer, J.; Brasseur, N.; Van Lier, J. E.; Lenearts, V.; Le Garrec, D.; Leroux, J. C. *J. Pharm. Pharmacol*. 2001, 53, 166.
21. Brinker, C. J.; Schrer, G. *Sol-Gel Science: The Physics and Chemistry of Sol-Gel Processing*; Academic Press: San Diedo, 1990, p-601.
22. Avnir, D. Braun, S.; Lev, O.; Ottolenghi, O. *Chem. Mater*. 1994, 6, 1605.
23. Weetal, H. H. *Biochim. Biophys. Acta*. 1970, 212, 1.
24. Jain, T. K.; Roy, I; De, T. K.; Maitra, A. N. *J. Am. Chem. Soc*. 1998, 120, 11092-11095.
25. Shimada, M.; Shoji, N.; Takahashi, A. *Anticancer Res*. 1995, 15, 109.

26. Lal, M.; Levy, L.; Kim, K. S.; He, G. S.; Wang, X.; Min, Y. H.; Pakatchi, S.; Prasad, P. N. *Chem. Mater.* 2000, 12, 2632-2639
27. Badley, R. D.; Warren, T. F.; McEnroe, F. J.; Assink, R. A. *Langmuir,* 1990, 6, 792-801
28. Nass, R.; Schmidt, H. *J. Non-Crys. Solids.* 1990, 121, 329
29. Arriagada, F. G.; Osseo-Asare, K. *J. Colloid Interface Sci.* 1995, 170, 8
30. Chang, C.; Fogler, H. S. *AICHE Journal.* 1996, 42, 3153
31. Hasan, T. *Photodynamic therapy: basic principals and clinical applications; Mercel Dekker: New York.* 1992, p-187.
32. Pandey, R. K.; Sumlin, A. B.; Potter, W. R.; Bellnier, D. A.; Henderson, B. W.; Constantine, S.; Aoudia, M.; Rodgers, M. R.; Smith, K. M.; Dougherty, T. *Photochem. Photobiol.* 1996, 63, 194-205.
33. Henderson, B. W.; Bellnier, D. A.; Graco, W. R.; Sharma, A.; Pandey, R. K.; Vaughan, L.; Weishaupt, K.; Dougherty, T. J. *Cancer Res.* 1997, 57, 4000-4007.
34. Frederiksen, P. K.; Jorgensen, M.; Ogilby, P. R. *J. Am. Chem. Soc.* 2001, 123, 1215-1221.
35. Karotki, A.; Kruk, M.; Drobizhev, M.; Rebane, A.; Nickel, E.; Spangler, C. W. *IEEE J. Quantum Electron.* 2001, 7, 971.
36. Lindig, B. A.; Rodgers, M. A. J.; Schaap, A. P. *J. Am. Chem. Soc.* 1980, 102, 5590-5593.
37. Mossman, T. *J. Immunol. Methods* 1983, 65, 55.
38. Gurfinkel, M.; Thompson, A. B.; Ralston, W.; Troy, T. L.; Moore, A. L.; Moore, T. A.; Gust, J. D.; Tatman, D.; Reynolds, J. S.; Muggenberger, B.; Nikula, K.; Pandey, R.; Mayer, R. H.; Hawrysz, D. J.; Sevick-Muraca, E. M. *Photochem. Photobiol.* 2000, 72, 94-102.
39. Levy, L.; Sahoo, Y.; Kim, K. S.; Bergey, E. J.; Prasad, P. N. *Chem. Mater.* Accepted (In Press).

The invention claimed is:

1. A method of preparing ceramic nanoparticles loaded with a photosensitive drug comprising the steps of:
   a) preparing micelles entrapping the photosensitive drug, wherein the photosensitive drug is 2-devinyl-2-(1-hexyloxyethyl) pyropheophorbide;
   b) adding alkoxyorganosilane to the micelles to form complexes of silica and the micelles;
   c) subjecting the complexes of silica and micelles to alkaline hydrolysis to precipitate silica nanoparticles in which the photosensitive drug molecules are entrapped; and
   d) isolating the precipitated nanoparticles after dialysis.

2. The method of claim 1, wherein the alkoxyorganosilane is triethoxyvinylsilane.

3. The method of claim 1, wherein the micelles comprise AOT and 1-butanol.

4. The method of claim 1, wherein the alkaline hydrolysis is carried out by ammonia.

5. The method of claim 1, wherein the alkaline hydrolysis is carried out by an ammonium compound.

* * * * *